United States Patent
Bahner

(10) Patent No.: US 8,750,968 B2
(45) Date of Patent: Jun. 10, 2014

(54) DEVICE AND PROCEDURE FOR THE DIAGNOSIS OR DIAGNOSTIC PREPARATION AND/OR THERAPY MONITORING OF INFLAMMATORY DISEASES SUCH AS RHEUMATOID ARTHRITIS

(75) Inventor: Malte Bahner, Berlin (DE)

(73) Assignee: MIVENION GmbH, Berlin (DE)

( * ) Notice: Subject to any disclaimer, the term of this patent is extended or adjusted under 35 U.S.C. 154(b) by 824 days.

(21) Appl. No.: 12/673,430

(22) PCT Filed: Aug. 14, 2008

(86) PCT No.: PCT/EP2008/060726
§ 371 (c)(1),
(2), (4) Date: Mar. 14, 2011

(87) PCT Pub. No.: WO2009/022003
PCT Pub. Date: Feb. 19, 2009

(65) Prior Publication Data
US 2011/0178397 A1    Jul. 21, 2011

(30) Foreign Application Priority Data

Aug. 14, 2007  (EP) .................................... 07114334
Mar. 13, 2008  (EP) .................................... 08004694

(51) Int. Cl.
*A61B 6/00*    (2006.01)
*A61B 19/00*   (2006.01)

(52) U.S. Cl.
USPC ............ 600/475; 600/473; 600/476; 128/897

(58) Field of Classification Search
USPC .................................. 128/897; 600/473, 476
See application file for complete search history.

(56) References Cited

U.S. PATENT DOCUMENTS 3,864,847 A * 2/1975 Friedman et al. ............... 34/202
5,567,409 A * 10/1996 Aizawa et al. ............. 424/9.363
(Continued)

FOREIGN PATENT DOCUMENTS

DE    100 04 989    10/2001
DE    102 20 955    12/2003
(Continued)

OTHER PUBLICATIONS

Hansch, Andreas et al. In Vivo Imaging of Experimental Arthritis With Near-Infrared Fluorescence. Arthritis & Rheumatism. vol. 50, No. 3, Mar. 2004, pp. 961-967.*

(Continued)

*Primary Examiner* — Long V. Le
*Assistant Examiner* — Helene Bor
(74) *Attorney, Agent, or Firm* — Millen, White, Zelano & Branigan, P.C.

(57) ABSTRACT

A first aspect of the invention relates to a device for a diagnosis and/or therapy monitoring of inflammatory diseases, such as rheumatoid arthritis. It comprises at least a rest or support device (1) for holding at least one extremity (11) of a person. Thereby, the support device has the task of facilitating the at least one extremity, preferably two extremities, for instance the two hands to be comfortably and immovably placed as long as possible. This support device can be provided with a rest with several accessories, such as indentations, bowl-like recesses, ridges, elastic or non-elastic straps and/or loops, etc. Furthermore, at least an excitation source (2) for at least partially illuminating one extremity at least with a radiation of defined excitation wavelength. Furthermore, at least an image sensor (3) is incorporated for capturing at least a reference signal from the extremity as well as several signals from the regions of medical interest (ROI) of the extremity (11). Moreover, a device according to the invena)

b)

schematic representation of possible ROI's tion comprises a comparator for comparing the reference signal with the signals from the regions of medical interest (ROI).

28 Claims, 7 Drawing Sheets

(56) References Cited

U.S. PATENT DOCUMENTS

| | | | |
|---|---|---|---|
| 6,320,931 B1 * | 11/2001 | Arnold | 378/56 |
| 6,490,339 B2 * | 12/2002 | Mitchell et al. | 378/62 |
| 2001/0037811 A1 | 11/2001 | Beuthan et al. | |
| 2005/0105078 A1 * | 5/2005 | Carver et al. | 356/71 |

FOREIGN PATENT DOCUMENTS

| | | |
|---|---|---|
| EP | 1743658 A1 * | 1/2007 |
| WO | WO-99 04683 | 2/1999 |
| WO | WO-2007 000349 | 1/2007 |

OTHER PUBLICATIONS

International Search Report for PCT/EP2008/060726 dated Nov. 12, 2008.

Skerl et al., "Evaulation of similarity measures for reconstruction-based registration in image-guided radiotherapy and surgery," International Journal of Radiation: Oncology biology physics, Jul. 1, 2006, vol. 65, No. 3, pp. 943-953.

Abraham-Fuchs Klaus, "Method for evaluating the distribution of scattered light resulting from the local transillumination of a living organism, by determining characteristic values," Data Supplied from the espacenet database—Worldwide, Publication Date: Feb. 4, 1999; English Abstract of WO- 99 04683.

Czenkusch Wulf, "Fluorescent imaging arrangement for in-vivo diagnosis of joint illnesses and inflammation, whereby a light source and filter are used to generate light with a wavelength in the near infrared region," Data Supplied from the espacenet database—Worldwide, Publication Date: Dec. 11, 2003; English Abstract of DE-10220955.

* cited by examiner

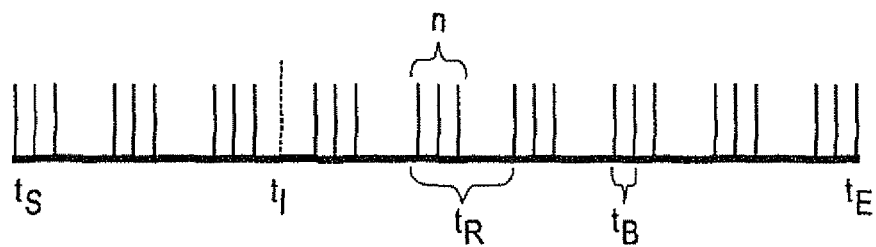

$t_S$: start of the measurement $t_I$ : time of injection of the dye, $t_I$ may also be before $t_S$ n : number of single measurement at a single measuring time, n is preferably between 1 and 20

$t_R$: interval between measuring times, wherein $t_R > (n+1) t_B$ $t_B$: interval between single measurements at a single measuring time $t_E$: end of measurement

Fig. 9

Time characteristics of signal acquisition with n = 3

DEVICE AND PROCEDURE FOR THE DIAGNOSIS OR DIAGNOSTIC PREPARATION AND/OR THERAPY MONITORING OF INFLAMMATORY DISEASES SUCH AS RHEUMATOID ARTHRITIS

The present invention pertains to a device and procedure for the diagnosis or diagnostic preparation and/or therapy monitoring of inflammatory diseases. A fluorescent dye is intravenously administered and the fluorescence of the dye is measured in all the interphalangeal articulations of the hand at different points of time following the administration. At least two measured fluorescent values that are selected from values pertaining to different points of time and/or tissue regions, as well as a mathematical correlation, which differentiates the diseased joints from the healthy ones for facilitating the diagnosis and/or therapy monitoring, are deduced from the measurements.

The diagnostic imaging is an integral part of the initial hypothesis and differential diagnosis of inflammatory diseases. In such diagnostic imaging, an important role is played by conventional X-ray and ultrasound processes, which make themselves apparent for example, in the recommendations of the American College of Rheumatologists (American College of Rheumatology Subcommittee on Rheumatoid Arthritis Guidelines. Arthritis & Rheumatism 46 (2002) 328), whereas functional procedures, which show an evidence of the activity of the disease are described for the magnetic resonance tomography (Reiser M F at al. Skeletal Radiology 18 (1989) 591), however on a semi-quantitative level as well as associated with a high degree of medical difficulty in the analysis of the images.

The application of optical techniques for the anatomical imaging of the joint regions using light scattering techniques (optical tomography) has been described. This procedure allows the imaging of anatomical structures, however fails to offer the possibility of accomplishing a quantitative comparison of the patients (Scheel at al. rheumatic Arthritis Rheumatoides 2002, 46, 1177) on account of the strong inter-individual or case-by-case variations in such structures. Another disadvantage of this method lies in the fact that the inflammatory synovia is not imaged. Further improvements showed that this technology can image sub-aspects of the rheumatoid arthritis (RA), however only one interphalangeal articulation of the hand is measured per examination. The examination of a hand that is affected by rheumatic arthritis (RA) is only possible by a successive measurement of all the interphalangeal articulations of the hand, which is very time-consuming and interferes in the use of contrast agents or makes it completely impossible. Since most of the contrast agents are very quickly eliminated, measurements at several joints would lead to very different final values (Scheel et al., Ann Rheum Dis 2005, 64, 239; US20010037811 A1). In addition, no dynamic data (circulation, distribution) can be recorded. Another disadvantage is the lack of a reference during the use of a contrast agent.

The use of fluorescent dyes as a contrast agent is described in the publications on the experimental trials on animals (W T Chen et al. (2005) Arthritis Res There. 7: R310; Hansch A. et al. (2004) Invest Radiol 39:626; Wunder A. et al. (2004) Arthritis Rheum. 50:2459). In these examples, the contrast agent is applied in such a manner that static signal differences are traced in a time span of 1 to a maximum of 24 hours after the application of the contrast agent. Areas that show a strong concentration at a predetermined point of time are suspicious RA sources. The used contrast agents are constituted in such a manner that they exhibit the largest possible signal difference after 3 hours, preferably 6 hours after the application. This process is however of minor importance in medical practice, since the examining doctor must quickly arrive at a diagnosis within 5 to 20 minutes after the start of the examination. The application of optical methods using the contrast agent indocyanine green (ICG) has been described for the human application in the case of diseased individuals (WO2007/000349). In this technique, the distribution of indocyanine green after the intravenous injection is traced at short time intervals using a camera. The measurement of a signal from a joint is accomplished in relation to a reference signal exterior to the hand of the patient. An arbitrary number of signal differences is traced at different monitoring points in relation to the reference. These signal differences are utilized for the diagnosis, i.e. the respective signal from a monitoring point of the hand is compared with an external reference signal. If this difference exceeds a predefined value, one can confirm the occurrence of a RA source. Although this process leads considerably faster to a result (within 10 to 20 min), it is associated with the disadvantage of low sensitivity and high case-by-case variation, and thus less suitable in medical practice, especially in the case of repeated check-ups of the same patient. Intra-individual variations are fluctuations of the measured values from one examination to the other on the same patient. These fluctuations are based upon the fact that the pharmacokinetics of ICG can distinctly vary from one examination to the other. These fluctuations have remarkably different causes and express themselves with a 1 to 50% variance of the maximum concentration in blood and the half-life period of elimination. This means that remarkably different signal intensities that are not associated with an altered RA activity can be measured above the relevant joints. As a result of these fluctuations, the threshold value for a signal difference must be very high in order to compensate the high intra-individual variations. The diagnostic procedure that is proposed in WO 2007/000349 is rendered insensitive by means of this process-relevant intervention technique. In the case of the avoidance of the scaling-up of the signal difference in order to measure further in the sensitive range, the risk of many healthy interphalangeal articulations of the hand being diagnosed as diseased increases. The publication WO2007/000349 and the mentioned preclinical efforts do not describe any process, which uses the signals of all the joints for devising a method that facilitates the detection of diseased joints and their differentiation from healthy joints. In particular, no solution that anticipates the subject of the present invention is described.

In general, a disadvantage of all the published procedures is the lack of clearly determinable values, which are independent of the intra-individual fluctuations of the applied contrast agent. This pertains not only to the initial and very sensitive diagnosis of inflammatory diseases, but also the differentiation of various inflammatory diseases from one another as well as other non-inflammatory diseases and in particular the quantitative assessment of the progression of an inflammatory disease under an initiated or continued therapy by means of differential diagnostic methods. This is particularly important because therapy monitoring has a growing importance in medical practice. The evaluation algorithms that are proposed by the known procedures especially have the disadvantage that the results can strongly fluctuate in the case of repeated examinations, which makes the therapy monitoring on the basis of the fluorescence measurement very difficult and uncertain. Overall, the evaluation algorithms that are proposed in WO2007/000349 are solely qualitative and unsuitable for a reliable therapy monitoring.

Methods for the semi-quantitative measurement of the accumulation of a contrast agent have been described in numerous publications for the measurement of contrast agents containing gadolinium in MRT (Hoffmann U et al. Magnetic Resonance Med. 33 (1995) 506) as well as for Doppler sonographic measurements of ultrasound contrast agents in the ultrasound imaging process (Fein M et al. Ultrasound Med Biol 21 (1995) 1013). Also, there are few publications on semi-quantitative measurement of the quantity of the contrast agent in computer tomography (Brix G et al. Radiology 210 (1999) 269). However, hardly any of these procedures is employed currently in the broad spectrum of clinical routine. The reasons for this are the computationally intensive evaluation procedures and the lack of broad availability.

Surprisingly, until now no quantitative or semi-quantitative evaluation procedures are described for the in vivo optical imaging, especially for inflammatory diseases including rheumatoid arthritis. The inventors hereby describe methods and procedures for quantitatively as well as semi-quantitatively evaluating the dispersion profile of the contrast agent in the patient within the framework of an optical imaging process.

It is therefore the underlying principle of the invention to improve upon the described state of the art and to find new ways to facilitate the diagnosis of RA in such a manner that an assessment of the progression of the disease is not only technically simple, but also possible in a short period of time.

Surprisingly, it has been found that a quantitative and semi-quantitative diagnosis of the RA with a high certainty is possible by means of the simultaneous measurement of the fluorescence signals above both hands and the application of a suitable evaluation method. The state-of-the-art technology is the fluorescence measurement technique that is proposed in WO2007/000349. This provides for the intravenous injection of ICG and the examination of the diseased hand. In case of a suspicion of the disease in the second hand, the publication WO2007/000349 suggests a further examination of this hand.

Surprisingly, the inventors observed that the examination of only one hand is associated with several disadvantages that are partly of uttermost importance. On the one hand, it is of primary concern to detect the onset of the disease well in advance, especially in the case of RA diagnosis. If the physician focuses only on the hand, in which the patient has complaints, the risk that he misses the minor rheumatic sources of the other hand that just begin to aggregate and not yet cause complaints. Thereby, the physician misses the point of time to initiate a therapy or to intensify an already existing therapy.

Another disadvantage of the procedure that is proposed in WO2007/000348 is based upon the fact that solely one hand can be examined after a single application of ICG, since the time-dependent profile of the fluorescence signals is only traced for a single hand. The inventors surprisingly observed that even a repeated application of ICG to examine the second, possibly diseased hand does not lead to the desired result. The reason for this lies in the different pharmacokinetics of the second ICG application, if it takes place in a time span of 60 min after the first application. Especially critical is a second injection of ICG within a lapse of 30 minutes or less after the first ICG application. Too high and spurious signals are measured after the second injection because the organs that facilitate elimination such as the liver are already saturated and the concentration levels of ICG that are still measurable in the blood are available. The observation that a repeated application of ICG to examine the second, possibly diseased hand is not possible, was surprising and unknown to date.

Subject of the invention is a method for the automated detection of suspicious RA sources and a method for comparing several examinations on a patient for the purpose of assessment of the progression of the RA. The significant task is to compute quantitative information that facilitate the physician to decide from a wide range of possible therapies. On account of the sophistications of an optical imaging that is supported by a contrast agent, procedures that are known until now are not suited for rendering a quantitative diagnosis that allow an assessment of the current activity of the disease. Particularly the blood kinetics of ICG that vary strongly from one examination to another prevented a comparison of the different examinations on the same patient until now.

The inventors could eliminate the disadvantage of the strong intra-individual variation in the procedure that is proposed in WO2007/000349 by the simultaneous measurement of the fluorescence signals above both hands. The subject of this invention is therefore a measurement procedure that is based on dynamic references. This measurement procedure has not been known to the state-of-the-art technology to date and can be implemented in the simultaneous measurement of the fluorescence signals above both the hands. It enables a high-quality and superior RA diagnosis, especially in the case of repeated examinations of the same patient. The advantage of the inventive process lies upon the fact that it is independent of the intra-individual fluctuations of the contrast agent. The inventive process of the dynamic reference measurement is based on interdependent mathematical correlations of the signal values that are measured at various points of time.

The invention is based on the task of providing an alternative or rather an improved device and procedure for the diagnosis or diagnostic preparation and/or therapy monitoring of inflammatory diseases such as rheumatoid arthritis.

This task is accomplished with the subject of the claims.

A first aspect of the invention relates to a device for a diagnosis and/or therapy monitoring of inflammatory diseases such as rheumatoid arthritis. It comprises at least a rest or a support device for holding at least one extremity of a person. This support device has thereby the task of allowing the extremity, preferably two extremities, namely two hands, to be fixed as long as possible in a comfortable position. This can be provided with a variety of accessories, such as indentations, bowl-like recesses, ridges, elastic or inelastic straps and/or loops, etc. Moreover, the device comprises at least one excitation source for the excitation or at least partial illumination of the extremity with at least one defined excitation wavelength. Furthermore, at least one image sensor is comprised for sensing at least one reference signal of the extremity and several signals from regions of medical interest (ROI) of the extremity (11). The device pertaining to the invention also comprises a comparator for comparing the reference signal with the signals from the regions of medical interest (ROI).

Alternatively, or in addition, the device can be provided with a rest for the illumination/scanning of at least one extremity, at least one excitation source of a defined excitation wavelength, an image sensor for simultaneous sensing of one or more reference signals along with signals from several regions of medical interest, whereby both the reference signal and the signals from the regions of medical interest originate from this extremity, as well as a comparator for the comparison of the reference signals with the signals from the regions of medical interest, whereby both the reference signal and the signals from the regions of medical interest originate from this extremity.

According to the invention, the term "region of interest" (ROI) designates the image area, which is particularly relevant in the image processing for the purpose of evaluation and in which an inflammatory disease such as RA is suspected. Alternatively, the acronyms AOI (Area of Interest) or WOI (Window of Interest) are also used in the literature.

According to the invention, the term "reference signal" refers to a signal of defined parameters, to which the signal values of the measuring device can be referred to.

Another aspect of the present invention relates to a device for an imaging-based diagnosis and/or therapy monitoring of inflammatory diseases such as rheumatoid arthritis, whereby the device comprises a housing with a rest or a support device for holding at least one extremity, preferably two extremities, further preferably two hands of a person. The support device can be hereby moved out of the housing and shifted back into the housing while holding the extremity. This enables a simple initial placement of the patient's hands on the support device, so that the patient can see his hands in the held position to make him feel mentally at ease. The hands are then moved into the housing with the support device.

The present invention also pertains to a device that combines the previously described aspects of the invention with one another.

It is preferred that the resting area comprises at least a dimension of 30 cm×20 cm for the simultaneous illumination/scanning of two extremities and that the image sensor with an illumination area of at least 30 cm×20 cm is suitable for the simultaneous detection of signals from two extremities.

It is preferred to have a homogeneous illumination, which irradiates the extremity in a large-area manner combined with sensing the working area at once or (alternatively) in a dot-wise manner combined with scanning the working area. Preferably at least two and more preferably up to four excitation sources are intended.

The excitation wavelength is preferably selected from the excitation wavelength range between 650 nm and 900 nm. Most preferably, the excitation wavelength ranges between 740 nm and 810 nm. In another preferred embodiment, besides the excitation source the device comprises a second excitation source with a wavelength ranging between 400 nm and 700 nm or 800 nm and 1000 nm, which irradiates or scans the extremities in a large-area or dot-wise manner.

The excitation source can be selected from the group comprising a laser, a laser diode, a LED and a polychromatic lamp with filters. The rest is preferably illuminated by the excitation source in a large-area and/or dot-wise manner and scanned over in a stepwise manner (raster-type scanning), LEDs (light-emitting diodes), laser, laser diodes and/or strong polychromatic light sources such as xenon lamps in combination with filters, which select a narrow wavelength range are preferred. The light sources are continuously emitting (continuous wave; CW) or pulsed (time-resolved measurement). Excitation wavelengths of the spectral range between 650 nm and 900 nm are preferred.

The image sensor of the invention-relevant device may be a CCD camera and/or CMOS camera, preferably with an image signal amplifier. Furthermore, a micro-channel plate and/or an electron-multiplying amplifier on a sensor chip are preferred.

The image sensor can also comprises a photodiode or avalanche photodiode with a dot-scanning mechanism. Furthermore, the image sensor can comprise a filter, preferably a long pass filter, which suppresses the reflected light of the excitation source at the excitation wavelengths to such an extent that it is weaker than the signals to be detected. The excitation source can thereby possess a filter, preferably a short pass filter, which suppresses the reflected light of the excitation source at the detection wavelengths to such an extent that it is weaker than the signals to be detected.

At least a second image sensor and/or a path deflector could be provided for at least another site of reception at the other side of the extremity.

The measurement at the inside of the hand allows for the determination of a so-called input function for the mathematical modelling of blood flow. From the measurement of the signals in the regions of medical interest, a mathematical model of blood flow and the input function, a diffusion coefficient can be determined for the intermediately lying tissue, whereby the diffusion coefficients for the infected and healthy tissues differ significantly from one another. Thereby a differentiation between infected and healthy rheumatic joints is likewise feasible.

The signals that are analogized by the comparator can be based upon the fluorescence of the administered dye. According to the invention, the comparator processes at least one or two reference signals, preferably at least eight reference signals. It is also preferred that the comparator mathematically processes the measured reference values in order to determine a general reference value. It is preferred that the comparator processes at least five signals from the regions of medical interest. Most preferably, the comparator processes 28 signals from the regions of medical interest.

The device can consecutively and repeatedly receive several signals at a cycle time $t_R$ of 20 milliseconds to 10 minutes, particularly preferred, 20 milliseconds to 5 seconds and most preferably, 100 milliseconds to 2 seconds (see FIG. 9). At any point of time, the signals can be measured several times, preferably 1 to 20 times at a cycle time of 1 millisecond to 1 second. Optionally instead of the n number of measurements at a single point of time, only the mean value of the n number of measurements is calculated. Several signals are received over a time period of 20 milliseconds up to 24 hours. Most preferably, the reception of signals is accomplished within a time period of 5 minutes to 20 minutes or preferably up to 10 minutes. The received signals are then processed by the comparator and compared.

The invention-relevant device may also be appropriate to determine at least one region of medical interest by means of a correlation coefficient of at least two combined, time-dependent signals, whereby the signals can originate from the same individual or two different individuals. A database can be formed and can be used as a basis for data synchronization.

Thus according to the invention, at least two measuring parameters are selected from values that are measured at different time points and/or different tissue regions for the purpose of carrying out a diagnosis and a mathematical correlation is formed between the parameters. The comparator can comprise a software, which also comprises an evaluation algorithm. The comparator accomplishes a mathematical correlation of the measuring parameters. Quotients, mathematical products, sums, and differentiations (standardized) as well as integrals are preferred. In a mathematical correlation of the measuring parameters from intensity values, the same can originate from measuring parameters that have been obtained at the same time or different points of time after the administration of the fluorescent dye. The measuring parameters from time courses can be combined with measuring parameters from intensity values at defined single points of time. The comparator can be suitable for processing the measured reference values through a mathematical modelling of the blood flow in one extremity, in order to determine a general reference value, preferably by means of at least a diffusion coefficient that represents a healthy and/or diseased extremity.

The comparator can be provided with output masks that assist a physician in the assessment of the severity of the disease.

The comparator can be equipped with a device, which captures the reflection image of the hand, in order to automatically determine the position of the ROI from this reflection image. For the purpose of determining the position of ROI, the contours of the hand are traced and optionally a reference point is fixed at the carpus by the evaluating person. The position of the ROI results from strictly-specified relative paths between the reference point at the carpus and the fingertip that is determined from the contour. The ROIs are laterally determined by means of the contour. Possibly the evaluating person can correct the position of ROI by using an appropriate software. The automatic choice of the position of the ROI is not a problem particularly after the ninetieth percentile is evaluated in the ROI.

The reflection image is preferably measured using an additional light source illuminating the extremity, whose wavelength lies in the wavelength range of the fluorescent emission, and thereby its light can pass unhindered through the long-pass filter in front of the image sensor. This light source is used only for capturing the reflection image, whereas it is not switched on while receiving the actual fluorescence signals.

The invention also refers to a procedure for the quantitative and semi-quantitative diagnosis or diagnostic preparation and/or therapy control of inflammatory diseases such as rheumatoid arthritis. For this purpose, the following steps are undertaken, whereby their sequence need not be specified. A fluorescent dye is perorally or parenterally administered to a patient. At least one extremity of a patient is inserted into or placed upon a device that has been described previously and/or henceforth. This is followed by an excitation of the fluorescence of the dye and a simultaneous measurement of the fluorescence of one or more reference signals and one or more signals from the region of medical interest of one or more of these extremities, whereby both the reference signal as well as the signal from the region of medical interest originate from this extremity. The reference signals are compared to the signals from the regions of medical interest in a comparator.

The invention also concerns a procedure for the capturing of a spatially two-dimensional fluorescence image and/or a preparation of the same comprising the steps: perorally or parenterally administrating of a fluorescent dye to a patient, positioning at least one extremity of a patient in a device that has been described previously and/or henceforth, exciting of the administered fluorescent dye at an excitation wavelength of 660 nm to 900 nm, and capturing of a spatially two-dimensional image of the fluorescence signal.

The two-dimensional image can also be obtained by scanning an area, whereby the measured values constitute the image.

Most preferably, two extremities are placed simultaneously upon the rest and at the same time the signals of both the extremities are measured and compared. Surprisingly it could be observed that only the simultaneous examination of both hands produces a sufficiently large number of mathematical correlations for healthy joints and possibly sick joints, and obtains to an improved result.

According to the invention, the fluorescent dye is a near-infrared dye that is preferably selected from the class of polymethine dyes. An indotricarbocyanine dye is the most preferred dye from the class of polymethine dyes. A particularly preferred dye is the fluorescent dye indocyanine green (ICG).

According to the invention, dyes with a high molar absorption coefficient or extinction coefficient in the spectral wavelength range from 650 nm to 950 nm are preferred as the fluorescent dye, particularly polymethine dyes with a molar absorption coefficient or extinction coefficient greater than 150,000 $cm^{-1}$ $M^{-1}$ in the spectral wavelength range from 700 nm to 900 nm. Preferred polymethine dyes are cyanine dyes, as described in WO2005/019247, WO2004/028449 and WO98/48846. The dyes and structures that were disclosed in these publications are the subject matter of the present disclosure.

Especially preferred are indotricarbocyanines, such as indocyanine green (ICG; cardiogreen). ICG is clinically approved and is used for the diagnostic imaging (WO2007/000349, Proc. Nat. Acad. Sci. USA 2000, 97, 2767, Semin. Ophthalmol. 1998, 13, 189). The use of ICG at a dose of 1 mg/kg body weight is especially preferred. An intravenous administration of the dye is preferred according to the invention.

According to the invention, the following measuring parameter can be measured and processed: fluorescence intensity, fluorescence ascent (slope of the signal ascent up to the maximum value of the fluorescence intensity), point of time or the time period for reaching the maximum fluorescence intensity, fluorescence descent (slope of the signal descent down to the minimum value of the fluorescence intensity), peak half width of the ascending and descending curve segments of the fluorescence, area under the ascending and descending curve segments of the fluorescence, integral of the ascending and descending curve segments of the fluorescence, determination of the mean values from various delay times of the temporal signal course. The entire curve trace can be used as an additional measuring parameter and can be described by using a mathematical adjustment (fit). The mathematical fit can be based upon a compartment model (Cuccia et al. Applied Optics 2003).

According to the invention, it is further preferred that several signals are consecutively captured many times at a cycle time of 0 minutes to 10 minutes and then processed and compared by the comparator. The measured values are preferably detected at different points of time after the application of the dye. In an embodiment of the invention, the measurements are based on the fluorescence of the administered contrast agent and include the measurement of fluorescence at different and arbitrary number of points of time after the administration. Result of the application of the light source and the fluorescent dye is a 20 image of the fluorescence distribution of the fluorescent dye over the entire area of both hands, at any point of time from 0 minutes to 20 minutes, 0 minutes to 15 minutes, 0 minutes to 10 minutes, 0 minutes to 5 minutes, 0 s to 120 s, 0 s to 60 s, 0 s to 30 s, 0 s to 20 s, 0 to 10 s after administration. A 2D image of the fluorescence distribution is preferably obtained at a cycle time of 5 seconds or less, particularly preferably at a cycle time of 2 s, most preferably at a cycle time of 1 s.

For the detection of RA two or more parameters are used for processing by an evaluation algorithm.

In a mathematical correlation of the measuring parameters from intensity values, the same can originate from measured parameters that are obtained at the same or different time points after administration of the fluorescent dye. Measured parameters from time courses can be combined with measured parameters from intensity values at defined single points of time.

All values are preferably measured simultaneously at both hands, all joints of both hands, and all other areas outside the joints or correspondingly both feet. Control areas or reference areas are areas of the hand (or correspondingly foot), which are no joints (finger pad, fingernail), as well as areas that are exterior to the hand (wrist, inner ear, other areas with superficial blood vessels) (or correspondingly foot). A representation of possible areas of medical interest and possible control areas can be seen in FIG. 2.

This means that preferably both the reference signal as well as the signal of the region of medical interest originate from one extremity. However, this is not necessarily the case. The reference signal may, for example, originate from the inner ear as outlined above.

28 measuring regions (ROI—regions of interest; regions of medical interest) are localized on the respective fingers and wrists of both the hands (or correspondingly foot) for the implementation of a preferred variant of the process pertaining to the invention. The ROIs are assigned to the DIP (distal interphalangeal articulation), the PIP (proximal interphalangeal articulation) and the MCP (metacarpophalangeal articulation) of the index finger, the middle finger, ring finger and the small finger. Two ROIs that represent the IP (interphalangeal articulation) and the MCP are attributed to the thumb. During the examination, the fluorescence activity is continuously measured at these ROI regions over a time period of 20 minutes after the injection of the contrast agent, for example, ICG injection, preferably up to 10 minutes after the injection of the contrast agent, for example, ICG injection. In the case of using a visual contrast agent, which specifically accumulates in the RA lesions after a time lapse of up to 24 hours after its application, the examination time can also be selected in such a manner that it represents the maximum accumulation.

It is known that the pharmacokinetics of a contrast agent such as ICG can sharply fluctuate in several independent examinations on the same patient. Surprisingly, it was possible to balance the intra-individual variations and facilitate a quantitative comparison of various examinations by means of the process according to the invention.

The present invention provides a procedure that is characterised by the fact that methods for the establishment of an internal measuring reference, automatic sighting of suspicious RA lesions and quantitative measurement of the progression of the RA disease severity are provided.

Surprisingly it has been found that the establishment of an internal measuring reference is an appropriate method for providing a quantitative measurement procedure. This method has not been known to the specialist until now. It has surprisingly been found that the fluorescence measurement of the finger nails is closely correlated with the concentration of the contrast agent in blood. At this point, the fluorescence signal is hardly attenuated. Another advantage are the anatomical and functional specialities of the blood flow in the finger, thereby firstly the fingertip and then the other sections of the finger are supplied with arterial blood. Another aspect of the process is the fact that the fingertip is not diseased with the RA. Thus a preferred area for the reference signals to be measured according to the invention is the mentioned ROI above the fingernails. A total of 8 ROIs according to the invention are defined above the finger nails, namely four ROIs, at each hand respectively. During the examination, the fluorescence activity is continuously measured in this ROI over a time period up to 20 minutes after the injection of the contrast agent, for instance, ICG injection, preferably up to 10 minutes after the injection of the contrast agent, for example, ICG injection. The ROIs are circular, oval or rectangular in shape. The determination of the signal intensity in the ROIs can be done by averaging the signal values of the pixels of the camera. The values are obtained with the units that are typical for CCD cameras (mV, random units, counts, cps or the like). The averaging of the pixel intensities or possibly a pixel binning can be employed. Percentile values are especially preferred, such as the ninetieth percentile, by means of which technical pixel errors (under- or over-amplifications) can be minimized.

The inventive process is characterized by the fact that the signal intensity in the ROI of the fingernails is processed by mathematical correlation. The determination of the time-dependent intensity curve that is measured as AUC (area under the curve) has proved to be suitable. Thereby, an AUC value is calculated for every ROI above the finger nails. Also suitable is the measurement of the maximum intensity and the point of time of the maximum intensity after the ICG injection. A measurement period of 20 s to 1200 s after the ICG injection has proved to be appropriate. A measuring period after the ICG Injection of 20 s to 600 a was suitable, a period of 20 s to 500 s was especially suitable and a period of 20 s to 300 a was particularly suitable. The obtained 8 AUG values of the fingernails are processed by mathematical correlation, in order to form an $AUC_{Ref}$ (AUG reference value). The formation of mean values from single AUG values has been proved to be appropriate. The formation of median values is likewise appropriate.

The mean $AUC_{Ref}$ value above the fingernails has been proved to be particularly suitable. A random error is ruled out to the greatest possible extent, since 8 ROIs are included in these values as well as the measurement period can be selected as long as desired.

A correction factor (CF) is determined after the calculation of the average $AUC_{Ref}$ value above the fingernails. The quotient of the mean $AUC_{Ref}$ value and the correction factor (CF) should result in a reference factor (RF) with a value of 100.

$$CF = \text{mean } AUC_{Ref}/100(RF)$$

$$100(RF) = \text{mean } AUC_{Ref}/CF$$

An internal measurement reference is provided with the help of this method.

The inventive process is further characterized by the fact that the signal intensity above the ROI of the interphalangeal articulations of the hand is measured and is processed by mathematical correlation. The ROI is thereby positioned above the DIP, PIP, IP and MCP. The determination of the time-dependent intensity curve that is measured as AUC (area under the curve) has proved to be suitable. An AUC value is thereby determined for every ROI above the interphalangeal articulations of the hands. The measurement of the maximum intensity and the point of time of the maximum intensity ICG injection. Also suitable is the measurement of the maximum intensity and the point of time of the maximum intensity after the ICG injection. A measurement period of 20 s to 1200 s after the ICG injection has proved to be appropriate. Particularly suitable time period was within 100 s to 600 a after the injection of the contrast agent, for example, ICG application.

Each of the obtained 28 AUC values of the interphalangeal articulations of the hands is processed by mathematical correlation. By dividing the AUC values by CF, corrected AUC values ($AUC_{corr}$) are obtained for the ROI above the respective interphalangeal articulations of the hands.

$$AUC_{corr} = AUC/CF$$

Surprisingly it has been shown that AUC values greater than 50, relative to the internal RF 100 indicate suspicious RA lesions. $AUC_{corr}$ values greater than 100, relative to the internal RF 100 were especially preferred. Healthy joints have an $AUC_{corr}$ value that is lesser than 50, relative to the internal RF 100 value. Thus a novel autonomous diagnostic algorithm was developed based on the procedure according to the invention.

The inventive process is further characterized by the layout of a method that allows the comparison of different examinations on the same patient. This method should compensate the different levels of the fluorescence signal intensity that result from the variable pharmacokinetics of ICG. The correction factor (CF) is calculated for each measurement leading to the formation of the signal intensity curve. Any number or any type of examinations can be assigned to one another by means of the CF of the ROI above the fingernails. Due to the division of the $AUC_{corr}$ values from an arbitrary examination by CF, they can be directly compared with other $AUC_{corr}$ values from previous examinations. The equation for calculating an arbitrary examination n is as follows:

$$AUC_{corr(n)} = AUC_{(n)} / CF_{(n)}$$

The value AKT for the time-dependent disease activity results from the possibility of direct comparability of the corrected AUC values. The formula for calculating the activity value AKT of any two examinations over time is as follows:

$$AKT = AUC_{corr(n)} / AUC_{corr(n-1)}$$

Values greater than 1 point out an increasing disease activity, respectively a deterioration of the result, whereas values less than 1 indicate an enhancement of the result, respectively a decrease in disease activity.

The administration of the contrast agent, for example indocyanine green can take place as a solution in distilled water at a dose of 0.1 mg/kg body weight. The extremities, such as the hands are placed in the measuring instrument, in concurrence with the injection of the contrast agent. Images are captured at cycle times of 3 s over a total time period of 10 minutes in an embodiment according to the invention.

In the present invention, a calculation of the absolute signal intensity above the individual joints is facilitated by the correction factors that are derived from the comparison of the mathematical correlations. The described procedure provides a quantitative and semi-quantitative diagnosis of RA and can therefore be considered to be superior to the procedures of the state of technology to date.

Another advantage according to the invention is that the intra-individual variations of the pharmacokinetics of the contrast agent (such as ICG) do not play a role in the dynamic reference measurement between the individual examinations, which makes this process especially suitable for the repeated examination for the purpose of therapy monitoring. Further advantages for the simultaneous examination of both hands are the shorter examination time, the avoidance of a second application of the contrast agent and the exclusion of sources of technical error, such as e.g. the altered measuring state or contrast agent kinetics. Furthermore, the subject of the present invention is the use of a polymethine dye in a process according to the invention. In particular, the subject of this invention is the use of an indotricarbocyanine dye in one of the procedures according to the invention. Most preferably is the use of ICG in a process according to the invention.

The present invention relates in a further aspect to a diagnostical composition comprising a fluorescent dye selected from the group comprising a polymethine dye, an indotricarbocyanine dye and ICG for the use in quantitative diagnosis of inflammatory diseases such as rheumatoid arthritis, the diagnosis comprising the steps of:

a. perorally or parenterally administrating of the diagnostical composition to a patient,
b. positioning of at least one extremity of a patient in a device,
c. excitating of the fluorescence of the dye,
d. simultaneously measuring of the fluorescence of one or more reference signals and one or more signals from the region of medical interest of this at least one extremity, whereby both the reference signal as well as the signal from the region of medical interest originate from this extremity, and
e. comparing of the reference signals with the signals from the regions of medical interest in a comparator.

Preferably said device is a device according to the present invention.

DESCRIPTION OF THE FIGURES

The figures show sample embodiments according to the invention.

FIG. 9 shows a model of the time characteristics of signal acquisition with n=3.

FIG. 1*a* represents a rest or support device 1 for holding at least one extremity 11 of a person. Both the hands 11 of a person are depicted in the embodiment. These hands 11 can be positioned by the support device 1 by means of 3D and/or 2D-structural elements. Such structural elements can be ridges, indentations and/or straps etc.

An excitation source 2, such as a laser diode with an optical fibre and a waveguide outlet 20 can be arranged in a known manner above or below the support device 1, in order to transmit a signal of defined excitation wavelength. An image sensor 3 for capturing reference signals and signals from the regions of medical interest can be positioned at the same side of the support device 1 as that of the excitation source 2. The support device should be diaphaneous for the signals or the reference signals respectively, for example, transparent or slightly diffusing, if the image sensor is arranged at the other side of the support device. One or more filters can be mounted between the image sensor 3 and the support device 1.

Figure 1:
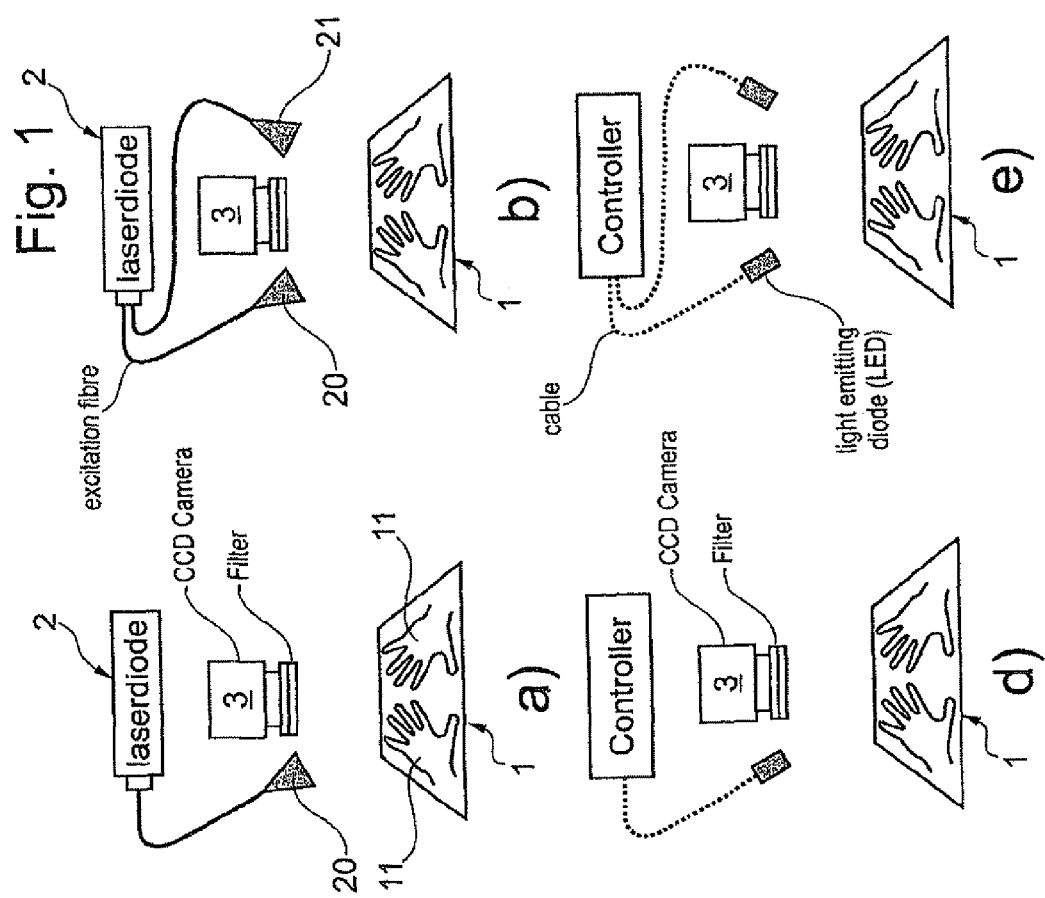
FIG. 1*a* shows a schematic of the embodiment of a device according to the invention.
FIG. 1*b* shows a schematic representation of another embodiment of the device according to the invention.
FIG. 1*c* shows a schematic representation of another embodiment of the device according to the invention.
FIG. 1*d* shows a schematic representation of another embodiment according to the invention.
FIG. 1*e* shows a schematic representation of another embodiment according to the invention.
FIG. 1*f* shows a schematic representation of another embodiment according to the invention.
Figure 1:
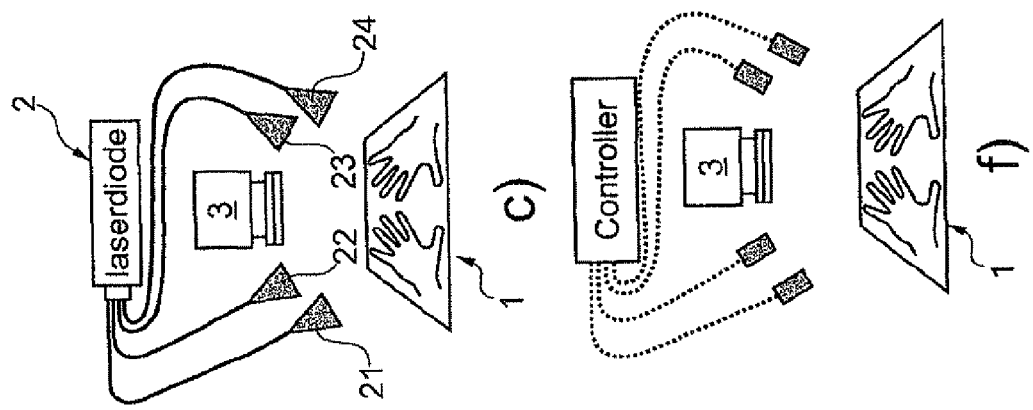
Figure 2:
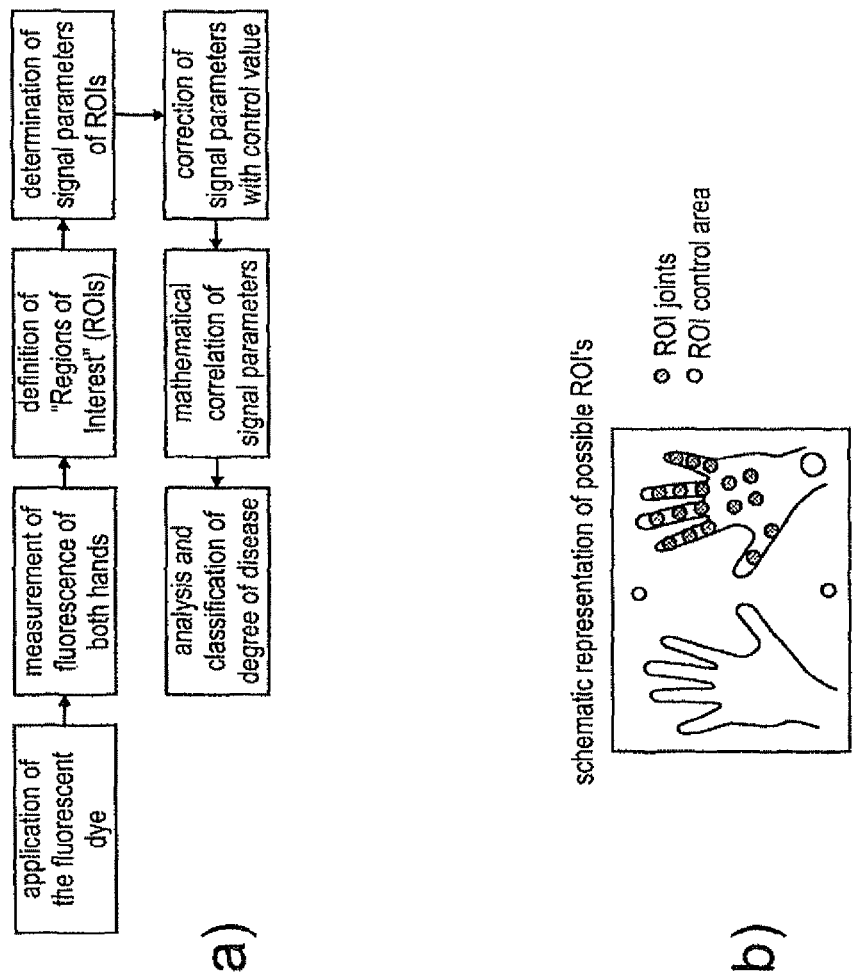
FIG. 2*a* shows a flow diagram of a process according to the invention.
FIG. 2*b* shows a schematic of possible regions of medical interest (regions of interest or ROIs)

Instead of the waveguide outlet 20, the second embodiment that is represented in FIG. 1b comprises another waveguide outlet 21 at another side of the image sensor 3. This facilitates the minimization of shadow formations. Four waveguide outlets 21-24 are shown in FIG. 1c in order to further improve the image quality. These waveguide outlets can be arranged around the image sensor 3 encircling the same. In the latter cases, all the waveguide exits 21-24 can be connected to a common excitation source 2, in this case, a laser diode.

Similarly designed layouts are depicted in the FIGS. 1d-f and only LEDs that are regulated by a common controller are intended. Other excitation sources can be considered.

Figure 4:
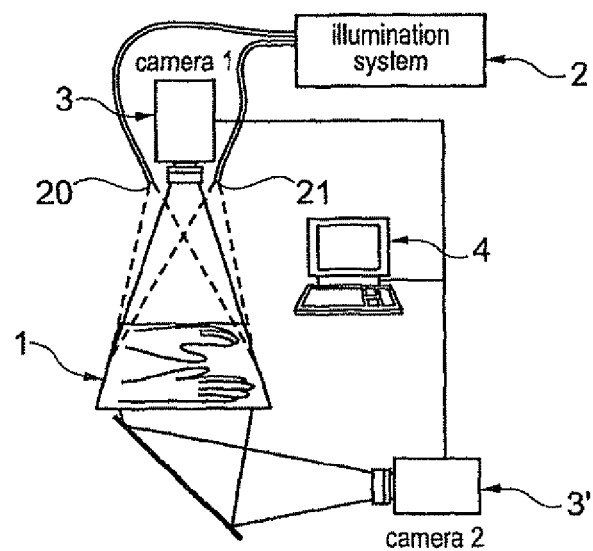
FIG. 4 shows an embodiment of a device according to the invention.

FIG. 4 represents an embodiment of a mechanism within or in conjunction with a device according to the invention. The mentioned layout is assigned with respect to the support device 1, excitation source 2 and the image sensor 3. Furthermore, a comparator 4, such as a computer 4, is represented. This receives the signals or the reference signals respectively that are captured by the image sensor 3 over a period of time and compares them to render results that facilitate the diagnostic and therapy monitoring process. Another image sensor 3' that captures additional signals or reference signals and likewise transmits them to the computer 4 is shown in the depicted embodiment.

Figure 5:
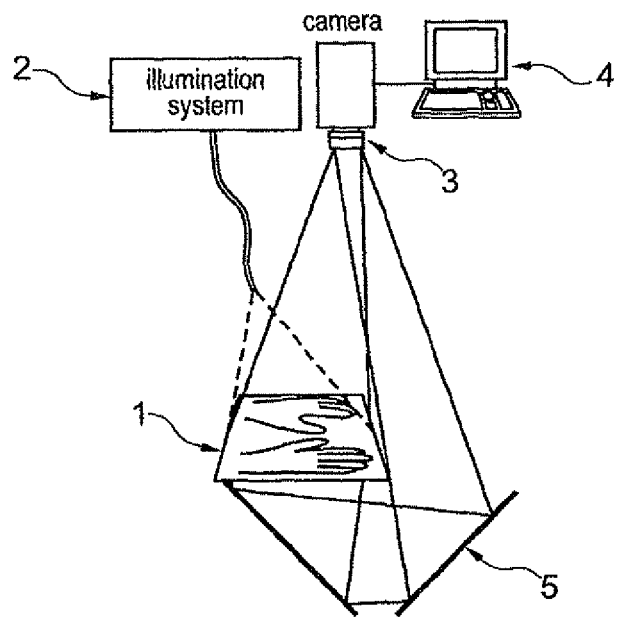
FIG. 5 shows another embodiment of a device according to the invention.

FIG. 5 shows a very similar setup with the exception that a path deflector 5, such as prisms and/or mirrors etc. is depicted instead of the additional image sensor 3', in order to capture signals from both sides of the support device.

Figure 6:
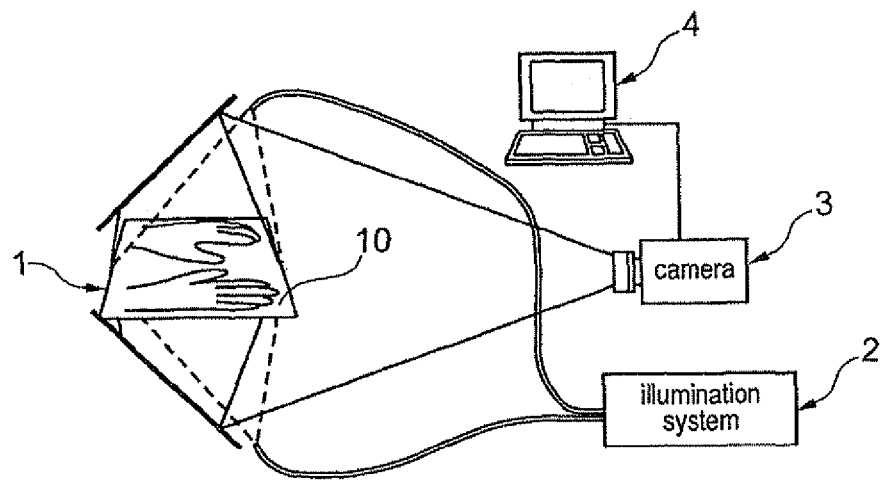
FIG. 6 shows another embodiment of a device according to the invention.

FIG. 6 shows an image sensor 3, which is placed essentially laterally to the support device 1 and receives the signals or reference signals from above and beneath the support device 1, whereby the signals are guided to the image sensor by means of appropriately designed path deflectors 5' and 5".

Figure 7:
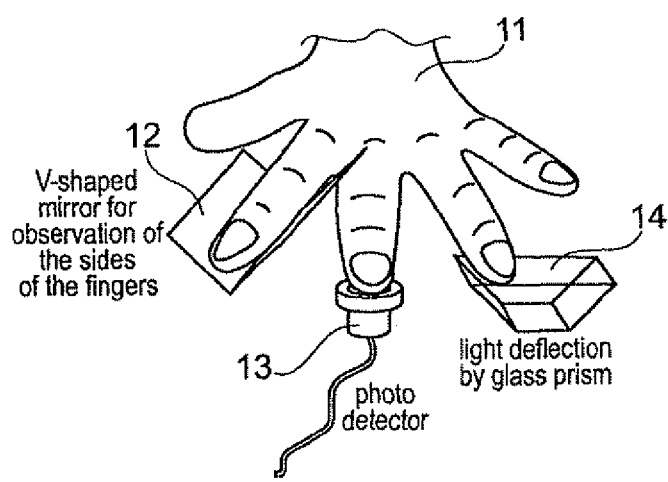
FIG. 7 shows an embodiment of a device according to the invention for capturing signals and/or reference signals, FIG. 8A+B shows a schematic of a remote device embodiment according to the invention

FIG. 7 shows many, however not all kinds of examples of additional or alternative image sensors. Towards the far left, a mirror setup 12 is shown that delivers a further improved image especially in the region of the joints by capturing signals even from their sides. Towards the far right, a prism 14 for light deflection is depicted, in order to deliver a signal even from beneath the support device (not shown) or rather from the hand 11 to the image sensor (not shown). At the centre, a photo-detector 13 is shown that captures the signals or reference signals for further evaluation as an example of an additional or alternative image sensor.

Figure 8B:
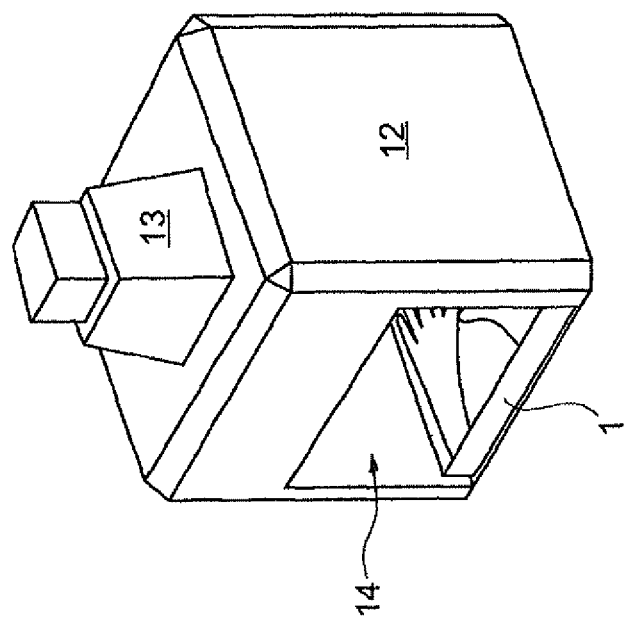
Figure 8A:
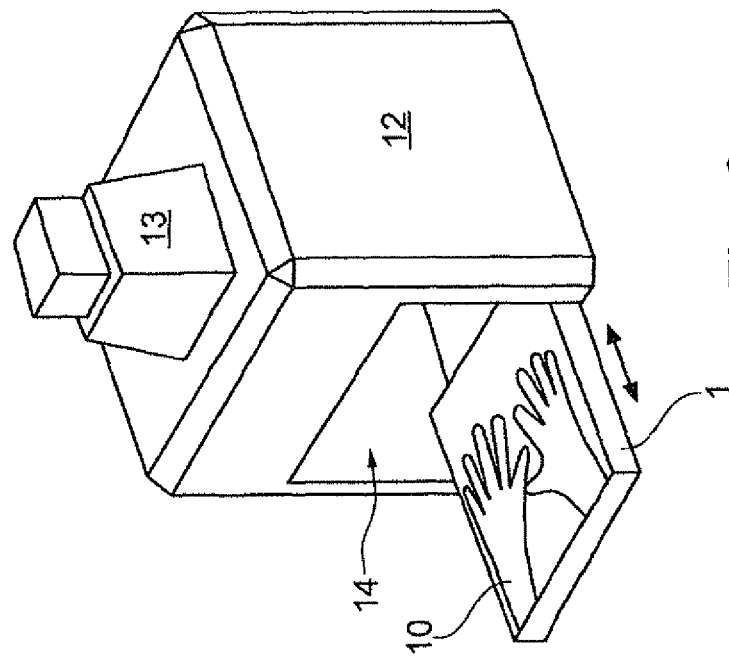

A housing 12 for the device or its components according to the invention is shown in FIG. 8A. The housing 12 can comprise auxiliary structures 13 for the accommodation of components, such as the image sensor (not shown). The housing 12 can comprise at least an opening or a recess 14, in which the support device 1 is placed. As pointed out by the arrows in the FIG. 8A, the support device can be moved out of the opening 14 in a linear manner. Both hands of a person can be placed on this support device 1 in the described position. Their position can be optimized by means of straps or indentations 10.

FIG. 8B shows the housing 12 with the support device 1 in an inserted state. The hands of a person are still present on this support device. The acquisition of the signals is accomplished at this position of the support device 1. The part of the opening that is opened towards the outside can be darkened with respect to the surroundings by appropriate means, such as one or more screens that are composed of appropriate, mostly dark materials or other light-proofing means.

EXAMPLES

The following examples shall explain the present invention in detail.

Example 1

Patient, male, 56 years, weight 78 kg. The clinical examination shows a painful inflammation of the joints DIP-L1, PIP-L1 and PIP-L2 of the left hand and PIP-R1 of the right hand. The patient is treated with antiphlogistic drugs only upon necessity at the time of the clinical examination.

Methods and implementation: Intravenous injection of indocyanine green (ICG pulsion) at a dose of 0.2 mg/kg. Bolus injection for about 5 s, the measurement time 0 corresponds to the termination of the Injection. Measuring device: simultaneous measurement of both the hands, illumination surface about 20 cm×30 cm, LEDs, excitation wavelength of 775 nm, detection >800 nm (2 long-pass interference filters, each of whose $\lambda_{50\%}$=800 nm), iCCD camera with standard lens (water/Peltier-type cooling).

Data collection (image capture) for both the hands up to 10 minutes after the injection with a cycle time of 3 s (20 frames/min).

Figure 3:
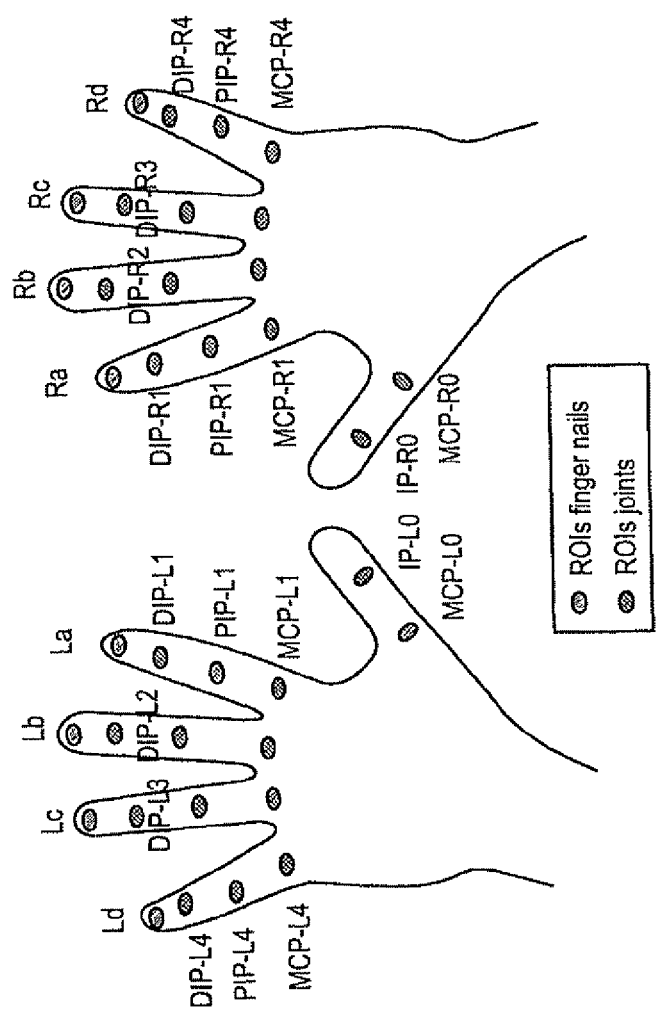
FIG. 3 shows a schematic of possible regions of medical interest in the hand and the interphalangeal articulations of the hands as well as the reference points in the fingertip regions.

Image Analysis:

Measurement strategy and position of the ROIs are shown in FIG. 3.

ROIs of the fingernails—shape: oval, width: 8 mm, height: 5 mm;

ROIs of the joints—shape: oval;

DIP—width: 8 mm, height: 5 mm;

PIP—width: 10 mm, height: 8 mm;

MCP—width: 10 mm, height: 8 mm;

ROIs of the thumb—shape: oval,

IP: width: 10 mm, height: 8 mm;

MCP—width: 12 mm, height: 10 mm;

Image analysis for the determination of $AUC_{Ref}$ of the finger nails: Determination of the AUC of the time-dependent profile of the signal intensities of the ROIs, starting from signal rise, about 20 s to 450 s in the finger nails (140 frames, starting from signal rise, about 20 s to 450 s, each with ninetieth percentile of the intensity values of the ROIs, random units).

| ROI | La | Lb | Lc | Ld | Ra | Rb | Rc | Rd |
| --- | --- | --- | --- | --- | --- | --- | --- | --- |
| AUC | 267800 | 245293 | 253933 | 232148 | 279954 | 249876 | 246173 | 231784 |

Mean $AUC_{Ref}$: 250870 (standard deviation: ±16522)

Image Analysis for the Determination of the AUC Value (Joints):

Determination of the AUC value from 60 s to 490 s in the ROIs of the fingernails (140 frames, 60 s to 490 s, each with ninetieth percentile of the intensity values of the ROIs, random units).

| ROI | DIP-L1 | DIP-L2 | DIP-L3 | DIP-L4 | IP-L0 | DIP-R1 | DIP-R2 | DIP-R3 | DIP-R4 | IP-R0 |
|---|---|---|---|---|---|---|---|---|---|---|
| AUC | 272101 | 155202 | 121954 | 103213 | 104123 | 112541 | 137651 | 101453 | 119832 | 92743 |
| $AUC_{corr}$ | 108 | 62 | 49 | 41 | 42 | 45 | 55 | 40 | 48 | 37 |

| | PIP-L1 | PIP-L2 | PIP-L3 | PIP-L4 | PIP-R1 | PIP-R2 | PIP-R3 | PIP-R4 |
|---|---|---|---|---|---|---|---|---|
| AUC | 280710 | 271785 | 95135 | 87890 | 131002 | 105169 | 91550 | 88560 |
| $AUC_{corr}$ | 112 | 108 | 38 | 35 | 52 | 42 | 36 | 35 |

| | MCP-L1 | MCP-L2 | MCP-L3 | MCP-L4 | MCP-L0 | MCP-R1 | MCP-R2 | MCP-R3 | MCP-R4 | MCP-L0 |
|---|---|---|---|---|---|---|---|---|---|---|
| AUC | 95673 | 139452 | 69845 | 80060 | 56196 | 98772 | 101260 | 68457 | 81705 | 88226 |
| $AUC_{corr}$ | 38 | 57 | 28 | 32 | 22 | 39 | 40 | 27 | 33 | 35 |

The values show that the measured $AUC_{corr}$ value coincide with the subjective pain sensation of the patient and the diagnosed inflammation. DIP-L1, PIP-L1 and PIP-L2 exhibit $AUC_{corr}$ values greater than 100. In addition, the joints DIP-L2 and MCP-L2 of the left hand, as well as DIP-R2 and PIP-R1 of the right-hand with values greater than 50 have been categorized as obvious. This result can be used as a useful criterion for the further assessment of the progression of the painful inflammation.

Example 2

Patient, female, 63 years, weight 59 kg. Patient with an acute progression of rheumatoid arthritis and damage to the joints DIP-R3, PIP-R3 and PIP-R4.

The patient was examined twice: the current examination as well as four weeks before the current examination. An intensive therapy using Infliximab® was administered upon the diagnosis of an activated rheumatoid arthritis four weeks before the current examination. The clinical examination currently shows an essentially unchanged result with only a low-level decline in the inflammation of the diseased joints. However, the patient reports an improvement in the subjective perception of the disease with a decline in the morning stiffness and the pain sensations.

Intravenous Injection of indocyanine green (ICG pulsion) at a dose of 0.2 mg/kg on two different days of examination at an interval of four weeks.

Implementation, Methodologies and Data Collection as in Example 1
ROIs of the fingernails—shape: oval, width: 7 mm, height: 5 mm;
ROIs of the joints—shape: oval;
DIP—width: 7 mm, height: 5 mm;
PIP—width: 8 mm, height: 7 mm;
MCP—width: 8 mm, height: 7 mm;
ROIs of the thumb—shape: oval;
IP—width: 9 mm, height: 7 mm;
MCP: width: 10 mm, height: 8 mm.

First Examination (4 Weeks Prior to the Current Examination)

Image Analysis for the Determination of the $AUC_{Ref}$ Value (Fingernails):
Determination of the AUC value of the time-dependent profiles of the signal intensities of the ROIs from 20 s to 300 s in the finger nails (93 frames, 20 s to 300 s, each with ninetieth percentile of the intensity values of the ROIs, random units).

| ROI | La | Lb | Lc | Ld | Ra | Rb | Rc | Rd |
|---|---|---|---|---|---|---|---|---|
| AUC | 220816 | 201245 | 230897 | 206995 | 216897 | 209553 | 236190 | 199890 |

Mean $AUC_{Ref}$: 214960 (standard deviation: ±13850)

Image analysis for the determination of the AUC values (joints): Determination of the AUC value from 20 s to 300 s in the ROIs of the fingernails (93 frames, 20 s to 300 s, each with ninetieth percentile of the intensity values of the ROIs, random units).

| ROI | DIP-L1 | DIP-L2 | DIP-L3 | DIP-L4 | IP-L0 | DIP-R1 | DIP-R2 | DIP-R3 | DIP-R4 | IP-R0 |
|---|---|---|---|---|---|---|---|---|---|---|
| AUC | 98700 | 77325 | 45789 | 69870 | 56764 | 76900 | 85903 | 229895 | 125702 | 10078 |
| $AUC_{corr}$ | 46 | 36 | 21 | 32 | 26 | 36 | 40 | 107 | 58 | 47 |

| | PIP-L1 | PIP-L2 | PIP-L3 | PIP-L4 | PIP-R1 | PIP-R2 | PIP-R3 | PIP-R4 |
|---|---|---|---|---|---|---|---|---|
| AUC | 65784 | 99563 | 98340 | 73218 | 80615 | 101965 | 235822 | 210256 |
| $AUC_{corr}$ | 31 | 46 | 46 | 34 | 38 | 47 | 110 | 98 |

| | MCP-L1 | MCP-L2 | MCP-L3 | MCP-L4 | MCP-L0 | MCP-R1 | MCP-R2 | MCP-R3 | MCP-R4 | MCP-L0 |
|---|---|---|---|---|---|---|---|---|---|---|

-continued

| | | | | | | | | | |
|---|---|---|---|---|---|---|---|---|---|
| AUC | 55674 | 64339 | 79851 | 87664 | 99986 | 82213 | 74538 | 55439 | 89005 | 10178 |
| $AUC_{corr}$ | 26 | 30 | 37 | 41 | 47 | 38 | 35 | 26 | 41 | 47 |

Second Examination (Current)

Image analysis for the determination of the $AUC_{Ref}$ value (fingernails): Determination of the AUC value of the time-dependent profile of the signal intensities of the ROIs from 20 s to 300 s in the finger nails (93 frames, 20 s to 300 s each with ninetieth percentile of the intensity values of the ROIs, random units).

| ROI | La | Lb | Lc | Ld | Ra | Rb | Rc | Rd |
|---|---|---|---|---|---|---|---|---|
| AUC | 200816 | 187245 | 210897 | 185949 | 202178 | 188680 | 219045 | 179270 |

Mean $AUC_{Ref}$: 196760 (standard deviation: ±13737)

In contrast to the measurement four weeks before the current examination, a 9.3% lower signal level (fluctuation in the ICG signal kinetics).

Image Analysis for Determination of the AUC Value (Joints):

Determination of the AUC value from 20 s to 300 s in the ROIs of the fingernails (93 frames, 20 s to 300 s, each with ninetieth percentile of the intensity values of the ROIs, random units).

| ROI | DIP-L1 | DIP-L2 | DIP-L3 | DIP-L4 | IP-L0 | DIP-R1 | DIP-R2 | DIP-R3 | DIP-R4 | IP-R0 |
|---|---|---|---|---|---|---|---|---|---|---|
| AUC | 78493 | 66341 | 41562 | 87098 | 45800 | 75135 | 82119 | 152175 | 110455 | 81655 |
| $AUC_{corr}$ | 40 | 34 | 21 | 44 | 23 | 38 | 42 | 77 | 56 | 41 |

| | PIP-L1 | PIP-L2 | PIP-L3 | PIP-L4 | PIP-R1 | PIP-R2 | PIP-R3 | PIP-R4 |
|---|---|---|---|---|---|---|---|---|
| AUC | 61238 | 65442 | 77658 | 70455 | 75440 | 72007 | 142236 | 175451 |
| $AUC_{corr}$ | 31 | 33 | 39 | 36 | 38 | 37 | 72 | 89 |

| | MCP-L1 | MCP-L2 | MCP-L3 | MCP-L4 | MCP-L0 | MCP-R1 | MCP-R2 | MCP-R3 | MCP-R4 | MCP-L0 |
|---|---|---|---|---|---|---|---|---|---|---|
| AUC | 54627 | 63463 | 80693 | 66836 | 93454 | 78658 | 65738 | 56120 | 73242 | 102347 |
| $AUC_{corr}$ | 28 | 32 | 41 | 34 | 47 | 40 | 33 | 29 | 37 | 52 |

The activity values AKT are calculated by dividing each of the corrected results of the initial examination by each of the corresponding corrected results of the second examination respectively.

Observation of the Symptomatic Joints:
DIP-R3: 0.71
PIP-R3: 0.65
PIP-84: 0.911

In this patient, the effectiveness of the ongoing intensified therapy using Infliximab® could be quantitatively demonstrated just after four weeks, irrespective of the contradictory results of the clinical examination.

Elements with which the present invention can be realized are for instance listed as follows:

Possible Camera Models as the Image Sensor:

| Model | manufacturer | type |
|---|---|---|
| sensicam em | PCO AG, Donaupark 11, 933309 | EMCCD |
| sensicam qe | Kelheim, Germany | CCD |

-continued

| Model | manufacturer | type |
|---|---|---|
| | The Cooke Corp., 6930 Metroplex Drive, Romulus, Michigan 48174, USA | |

-continued

| Model | manufacturer | type |
|---|---|---|
| $iXon^{EM}$ + DU-897 | Andor Technology PLC, 7 Millenium way, Springvale Business Park, Belfast, BT12 7AL, NORTHERN IRELAND | EMCCD |
| $iXon^{EM}$ + 885 | | EMCCD |
| $Luca^{EM}$ DL658M | | EMCCD |

-continued

| Model | manufacturer | type |
|---|---|---|
| PI-MAX: 512 | Princeton Instruments Inc., 3660 Quakerbridge Road, Trenton, NJ 08619, USA | MCP + CCD(ICCD) |
| PhotonMAX: 512B | | EMCCD |
| Pixis 512B | | CCD |
| CoolSnap ES2 | Photometrics, 3440 East Britannia Drive, Tucson, AZ 85706, USA | CCD |
| Cascade: 1K | | EMCCD |

Possible Sources of Illumination

| Type | Manufacturer |
|---|---|
| Laser diode | LDX Optronics, Inc., 1729 Triangle Park Drive, Maryville, TN 37801, USA |
| Laser diode | Applied Optronics - A Division of Candela, 111 Corporate Boulevard, Building J, South Plainfield, NJ 07080, USA |
| Laser diode | eagleyard Photonics GmbH, Rudower Chaussee 29, 12489 Berlin, Germany |

-continued

Type | Manufacturer
--- | ---
Laser diode | High Power Devices, Inc., 1200A Airport Rd., North Brunswick, NJ 08902, USA
LED | OSRAM Opto Semiconductors GmbH, Wernerwerkstrasse 2, D-93049 Regensburg, Germany
LED | Marubeni America Corporation, 3945 Freedom Circle, Suite 1000, Santa Clara, CA 95054, USA Possible Photodiodes as Image Sensors Type | Manufacturer
--- | ---
SAE500NS, SAR500 | LaserComponents GmbH, Werner-von-Siemens-Str. 15, 82140 Olching, Germany
S9251-15 | HAMAMATSU PHOTONICS K.K., 325-6, Sunayama-cho, Naka-ku, Hamamatsu City, Shizuoka Pref., 430-8587, Japan
Si avalanche photodiode KPDA050 | 949-2 Ebisu-cho, Fushimi-ku, Kyoto-shi, 612-8201 Japan Possible Manufacturers of Optical Filters Newport Corporation - Corion Filters, 8 E. Forge Parkway, Franklin, MA 02038, USA
Omega Optical, Inc., Delta Campus, Omega Drive, Brattleboro, VT 05301
LOT-Oriel GmbH & Co. KG, Im Tiefen See 58, D-64293 Darmstadt, Germany
Filtech Photonics Co. Ltd., Longcheng Industrial Park, Building # 3, 1st Floor West, Central Town, Longgang District, Shenzhen, China 518172

The disclosure contents of the previously discussed state of the art is included for the implementation of the individual aspects of the present invention.

The invention likewise includes individual features in the figures, even if they are showed there in the context of other features and/or are neither mentioned herein above nor herein below.

The invention likewise includes embodiments with any combination of features, which are shown or mentioned either prior to or after the various embodiments.

The invention likewise includes the accurate or exact expressions, features, numerical values or ranges, etc., if these expressions, features, numerical values or ranges were previously or subsequently mentioned in association with the expressions such as e.g. "more or less, or about, approximately, essentially, in general, at the lowest, at least" etc. (i.e. "about 3" would mean "3" or "essentially radial" would likewise mean "radial"). Moreover the expression "or/or rather" means "and/or".

The invention claimed is:

1. A device for a diagnosis and/or therapy monitoring of inflammatory diseases, comprising:
   at least a housing with a rest or a support device (1) for holding two extremities (11) of a person,
   at least one excitation source (2) for at least partially illuminating (11) with radiation of at least one defined excitation wavelength, wherein said excitation wavelength is selected from the wavelength range of 650 nm to 900 nm,
   at least one image sensor (3) for capturing at least one reference signal from at least one of said two extremities (11) and a plurality of signals from the regions of medical interest (ROI) of at least one of said two extremities (11), and
   a comparator (4) for comparing said at least one reference signal with the plurality of signals from the regions of medical interest (ROI), wherein said comparator (4) is configured to compare an area under the curve value (AUC value) from said at least one reference signal to determine a mean AUC reference value (mean $AUC_{REF}$) and a correction factor (CF) from the equation 100=mean $AUC_{REF}$/CF, and an area under the curve value, determined for each of said plurality of signals from the regions of medical interest (ROI), and a corrected AUC value ($AUC_{CORR}$ value) is then determined for each of said plurality of signals from the regions of medical interest (ROI) using the equation $AUC_{CORR}$=AUC/CF, and the $AUC_{CORR}$ value can be used to diagnose and/or therapy monitor the inflammatory diseases,
   wherein both said at least one reference signal and said plurality of signals from the region of medical interest originate from one extremity, and
   wherein the device is suitable for comparing the detected signals on the basis of the fluorescence of an administered dye by means of the comparator (4).

2. A device according to claim 1, wherein said support device (1) can additionally be moved out of the housing and moved back into the housing with the held extremities (11).

3. The device according to claim 2, wherein said at least one defined excitation wavelength is selected from the wavelength range of 740 nm to 810 nm.

4. The device according to claim 1, wherein said at least one defined excitation wavelength is selected from the wavelength range of 740 nm to 810 nm.

5. The device according to claim 1, wherein, besides said excitation source (20), the device further comprises a second excitation source (21) with a wavelength ranging between 400 nm and 700 nm.

6. The device according to claim 5, wherein said second excitation source (21) has a wavelength ranging between 800 nm and 1000 nm.

7. The device according to claim 5, wherein said second excitation source (21) can be activated for capture of a reflection image and can be deactivated during reception of the fluorescence signals.

8. The device according to claim 1, wherein said at least one image sensor (3) is a CCD and/or CMOS camera.

9. The device according to claim 1, wherein said at least one image sensor (3) comprises a photodiode or avalanche photodiode with a dot-scanning mechanism.

10. The device according to claim 1, wherein said at least one image sensor (3) comprises a filter which suppresses the reflected light of said at least one excitation source (2) at the excitation wavelengths to such an extent that it is weaker than the signals to be detected, and said at least one excitation source (2) comprises a filter which suppresses the reflected light of said at least one excitation source (2) at the detection wavelengths to such an extent that it is weaker than the signals to be detected.

11. The device according to claim 1, wherein said at least one excitation source (2) is a laser, laser diode, LED or polychromatic lamp with filters.

12. The device according to claim 1, wherein the device comprises at least a second image sensor (3') and/or a path deflector (5) for at least a further imaging of another side of at least one of said two extremities (11).

13. The device according to claim 1, wherein the comparator (4) processes at least two reference signals.

14. The device according to claim 1, wherein the comparator (4) processes eight reference signals.

15. The device according to claim 1, wherein the comparator (4) is suitable for processing the measured reference values through a mathematical modeling of the blood flow in one extremity, in order to determine a general reference value.

16. The device according to claim 1, wherein the comparator (4) processes at least five signals from the regions of medical interest (ROI).

17. The device according to claim 1, wherein the device is suitable for periodically receiving several signals over a time period of 5 minutes to 20 minutes and at a cycle time of 20 milliseconds to 10 minutes, whereby the imaging of a signal consists of the averaging of 1 to 20 individual signals at a cycle time of 1 ms to 1 second.

18. The device according to claim 1, wherein the device is capable of imaging a mean value of n number of measurements at a point of time 1 as well as a mean value of m number of measurements at a point of time 2, and then compare the measurements with the help of the comparator, whereby the measurements lie within the time period of 10 seconds to 20 minutes.

19. The device according to claim 1, wherein the device is adapted to determine at least one region of medical interest by means of a correlation coefficient of at least two combined, time-dependent signals, whereby the signals can originate from the same individual or two different individuals.

20. The device according to claim 1, wherein the device comprises a component for light-proofing the support device (1) with and without extremities laid upon (11) said support device.

21. The device according to claim 1, wherein the support device (1) comprises at least a minor (12), a photo-detector (13) and/or a path deflector (14) for at least one of said two extremities (11) and/or for each finger of at least one of said two extremities (11).

22. The device according to claim 1, wherein said two extremities are the two hands of said person.

23. The device according to claim 1, wherein said at least one image sensor (3) is a CCD and/or CMOS camera with a micro-channel plate and/or an electron-multiplying amplifier on the sensor chip.

24. The device according to claim 1, wherein said at least one image sensor (3) comprises a long-pass filter which suppresses the reflected light of said at least one excitation source (2) at the excitation wavelengths to such an extent that it is weaker than the signals to be detected, and said at least one excitation source (2) comprises a short-pass filter which suppresses the reflected light of said at least one excitation source (2) at the detection wavelengths to such an extent that it is weaker than the signals to be detected.

25. A method for the imaging of a spatially two-dimensional fluorescent image and/or preparation of the same, comprising:
    a. per orally or parenterally administering a fluorescent dye to a patient,
    b. positioning of said two extremities of a patient into a device according to claim 1,
    c. exciting the administered fluorescent dye with a radiation of excitation wavelength of 650 nm to 900 nm using said at least one excitation source of said device, and
    d. imaging of a spatially two-dimensional image of the fluorescence signal using said at least one image sensor and said comparator of said device.

26. A method according to claim 25, wherein the fluorescent dye is a near-infrared dye from the class of polymethine dyes.

27. A method according to claim 25, wherein the fluorescent dye is an indotricarbocyanine dye.

28. A method according to claim 25, wherein the fluorescent dye is indocyanine green (ICG).

* * * * *